(12) United States Patent
Rogers et al.

(10) Patent No.: US 10,195,000 B2
(45) Date of Patent: Feb. 5, 2019

(54) FEMALE LUER CONNECTOR DISINFECTING CAP

(71) Applicant: 3M INNOVATIVE PROPERTIES COMPANY, Saint Paul, MN (US)

(72) Inventors: Bobby E. Rogers, San Diego, CA (US); Gino Kang, Irvine, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 142 days.

(21) Appl. No.: 15/427,520

(22) Filed: Feb. 8, 2017

(65) Prior Publication Data

US 2017/0143447 A1 May 25, 2017

Related U.S. Application Data

(60) Continuation of application No. 14/285,526, filed on May 22, 2014, now abandoned, which is a division of application No. 13/099,324, filed on May 2, 2011, now Pat. No. 9,259,284.

(60) Provisional application No. 61/330,243, filed on Apr. 30, 2010.

(51) Int. Cl.
| | |
|---|---|
| *A61B 90/70* | (2016.01) |
| *A61M 39/20* | (2006.01) |
| *A61M 39/16* | (2006.01) |
| *B08B 1/00* | (2006.01) |
| *B08B 3/08* | (2006.01) |

(52) U.S. Cl.
CPC .............. *A61B 90/70* (2016.02); *A61M 39/16* (2013.01); *A61M 39/20* (2013.01); *B08B 1/003* (2013.01); *B08B 3/08* (2013.01); *A61M 39/162* (2013.01)

(58) Field of Classification Search
None
See application file for complete search history.

(56) References Cited

U.S. PATENT DOCUMENTS

| | | | |
|---|---|---|---|
| 1,744,026 A | 1/1930 | Baltzley | |
| 1,841,597 A | 1/1932 | Hammer et al. | |
| 1,937,492 A | 11/1933 | Merolle | |
| 2,322,701 A | 6/1943 | Nesset et al. | |
| 2,341,285 A | 2/1944 | Petrullo | |

(Continued)

FOREIGN PATENT DOCUMENTS

| | | | |
|---|---|---|---|
| DE | 2164821 A1 | 8/1972 | |
| EP | 0462355 A1 | 12/1991 | |

(Continued)

OTHER PUBLICATIONS

U.S. Appl. No. 60/815,806, filed Jun. 22, 2006, Anderson et al.

(Continued)

*Primary Examiner* — Eric W Golightly

(57) ABSTRACT

A cleaning device for a medical implement such as a female Luer connector. The cleaning device includes a cap having an interior cavity and an opening adapted to receive a site of the medical implement. The interior cavity is defined by an interior wall that includes a male Luer protrusion extending in the direction of the opening from an end of the interior cavity opposite the opening. A skin of cleaning material overlies at least a portion of the interior wall. The cleaning material may be pre-loaded with a cleaning agent and is adapted to clean the site of the medical implement.

20 Claims, 4 Drawing Sheets

(56) References Cited

U.S. PATENT DOCUMENTS

| | | |
|---|---|---|
| 2,731,963 A | 1/1956 | Blank |
| 2,740,480 A | 4/1956 | Cox et al. |
| 2,993,612 A | 7/1961 | Trautvetter |
| 3,120,879 A | 2/1964 | Warner |
| 3,199,748 A | 8/1965 | Bross |
| 3,362,587 A | 1/1968 | Postel et al. |
| 3,391,847 A | 7/1968 | Christine et al. |
| 3,405,831 A | 10/1968 | Hudson et al. |
| 3,431,548 A | 3/1969 | Busier et al. |
| 3,435,978 A | 4/1969 | Wittwer |
| 3,443,686 A | 5/1969 | Raymond et al. |
| 3,651,972 A | 3/1972 | Itoh |
| 3,771,685 A | 11/1973 | Micallef |
| 3,818,627 A | 6/1974 | Lebensfeld |
| 3,979,001 A | 9/1976 | Bogert |
| 3,987,921 A | 10/1976 | Aichinger |
| 3,987,930 A | 10/1976 | Fuson |
| 4,089,463 A | 5/1978 | Babiol |
| 4,169,751 A | 10/1979 | Yen |
| 4,232,677 A | 11/1980 | Leibinsohn |
| 4,257,526 A | 3/1981 | Weits et al. |
| 4,280,632 A | 7/1981 | Yuhara |
| 4,289,248 A | 9/1981 | Lynn |
| 4,335,756 A | 6/1982 | Sharp et al. |
| 4,340,148 A * | 7/1982 | Beckham ............ A61M 1/3627 215/247 |
| 4,401,227 A | 8/1983 | Pehr |
| 4,432,764 A | 2/1984 | Lopez |
| 4,440,207 A | 4/1984 | Genatempo et al. |
| 4,461,394 A | 7/1984 | Sendel et al. |
| 4,530,726 A | 7/1985 | Montiel |
| 4,564,116 A | 1/1986 | Prohaska |
| 4,572,373 A | 2/1986 | Johansson |
| 4,597,758 A | 7/1986 | Aalto et al. |
| 4,624,664 A | 11/1986 | Peluso et al. |
| 4,655,762 A | 4/1987 | Rogers |
| 4,671,306 A | 6/1987 | Spector |
| 4,674,643 A | 6/1987 | Wilde et al. |
| 4,712,705 A | 12/1987 | Fuehrer |
| 4,752,983 A | 6/1988 | Grieshaber |
| 4,778,447 A | 10/1988 | Velde et al. |
| 4,798,303 A | 1/1989 | Arnold |
| 4,810,241 A | 3/1989 | Rogers |
| 4,991,629 A | 2/1991 | Ernesto et al. |
| 5,065,783 A | 11/1991 | Ogle, II |
| 5,078,693 A | 1/1992 | Shine |
| 5,143,104 A | 9/1992 | Iba et al. |
| 5,169,033 A | 12/1992 | Shay |
| 5,184,742 A | 2/1993 | DeCaprio et al. |
| 5,242,425 A | 9/1993 | White et al. |
| 5,263,606 A | 11/1993 | Dutt et al. |
| 5,277,311 A | 1/1994 | Hollister |
| 5,292,020 A | 3/1994 | Narin |
| 5,385,372 A | 1/1995 | Utterberg |
| 5,385,378 A | 1/1995 | Hakamada et al. |
| 5,398,837 A | 3/1995 | Degrassi |
| 5,409,471 A | 4/1995 | Atkinson et al. |
| 5,445,270 A | 8/1995 | Dratz |
| 5,535,771 A | 7/1996 | Purdy et al. |
| 5,554,135 A | 9/1996 | Menyhay |
| 5,624,402 A | 4/1997 | Imbert |
| 5,694,978 A | 12/1997 | Heilmann et al. |
| 5,702,017 A | 12/1997 | Goncalves |
| 5,743,884 A | 4/1998 | Hasson et al. |
| 5,743,894 A | 4/1998 | Swisher |
| 5,792,120 A | 8/1998 | Menyhay |
| 5,807,345 A | 9/1998 | Grabenkort |
| 5,807,347 A | 9/1998 | Bonaldo |
| 5,947,954 A | 9/1999 | Bonaldo |
| 5,951,519 A | 9/1999 | Utterberg |
| 5,954,957 A | 9/1999 | Chin-Loy et al. |
| 5,989,227 A | 11/1999 | Vetter et al. |
| 6,004,299 A | 12/1999 | Arai et al. |
| 6,027,482 A | 2/2000 | Imbert |
| 6,036,672 A | 3/2000 | Allen et al. |
| 6,045,539 A | 4/2000 | Menyhay |
| 6,102,223 A | 8/2000 | Montgomery |
| 6,116,468 A | 9/2000 | Nilson |
| 6,190,364 B1 | 2/2001 | Imbert |
| 6,196,998 B1 | 3/2001 | Jansen et al. |
| 6,227,391 B1 | 5/2001 | King |
| 6,250,315 B1 | 6/2001 | Ernster |
| 6,293,293 B1 | 9/2001 | Wrigley et al. |
| 6,299,131 B1 | 10/2001 | Ryan |
| 6,364,862 B1 | 4/2002 | Bonilla |
| 6,394,983 B1 | 5/2002 | Mayoral et al. |
| 6,520,935 B1 | 2/2003 | Jansen et al. |
| 6,523,686 B1 | 2/2003 | Bae |
| 6,524,295 B2 | 2/2003 | Daubert et al. |
| 6,527,751 B2 | 3/2003 | Fischer et al. |
| 6,622,882 B2 | 9/2003 | Smith |
| 6,821,267 B2 | 11/2004 | Veillon, Jr. et al. |
| 6,880,801 B2 | 4/2005 | Matkovich et al. |
| 6,911,025 B2 | 6/2005 | Miyahara |
| 6,913,157 B2 | 7/2005 | Oh |
| 7,083,605 B2 | 8/2006 | Miyahara |
| 7,090,191 B2 | 8/2006 | Matkovich et al. |
| 7,118,560 B2 | 10/2006 | Bonaldo |
| 7,188,623 B2 | 3/2007 | Anderson et al. |
| 7,198,611 B2 | 4/2007 | Connell et al. |
| 7,282,186 B2 | 10/2007 | Lake, Jr. et al. |
| 7,316,669 B2 | 1/2008 | Ranalletta |
| 7,329,235 B2 | 2/2008 | Bertron et al. |
| 7,329,249 B2 | 2/2008 | Bonaldo |
| 7,427,275 B2 | 9/2008 | DeRuntz et al. |
| 7,452,349 B2 | 11/2008 | Miyahara |
| 7,500,964 B2 | 3/2009 | Shaw et al. |
| 7,530,977 B2 | 5/2009 | Lodi |
| 7,682,561 B2 | 3/2010 | Davis et al. |
| 7,704,002 B2 | 4/2010 | Fisher et al. |
| 7,780,794 B2 | 8/2010 | Rogers et al. |
| 7,857,793 B2 | 12/2010 | Raulerson et al. |
| 7,922,701 B2 | 4/2011 | Buchman |
| 7,931,618 B2 | 4/2011 | Wyrick |
| 7,931,877 B2 | 4/2011 | Steffens et al. |
| 7,967,779 B2 | 6/2011 | Bertron et al. |
| 7,985,302 B2 | 7/2011 | Rogers et al. |
| 7,988,676 B1 | 8/2011 | Gray |
| 8,061,544 B2 | 11/2011 | Frishman |
| 8,065,773 B2 | 11/2011 | Vaillancourt |
| 8,105,293 B2 | 1/2012 | Pickhard |
| 8,162,899 B2 | 4/2012 | Tennican |
| 8,167,847 B2 | 5/2012 | Anderson et al. |
| 8,172,813 B2 | 5/2012 | Janish |
| 8,177,768 B2 | 5/2012 | Leinsing |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,277,422 B2 | 10/2012 | Oliver et al. |
| 8,287,491 B2 | 10/2012 | Burns et al. |
| 8,296,893 B2 | 10/2012 | Vinci et al. |
| 8,303,548 B2 | 11/2012 | Ito et al. |
| 8,622,995 B2 | 1/2014 | Ziebol |
| 8,622,996 B2 | 1/2014 | Ziebol |
| 8,641,681 B2 | 2/2014 | Solomon et al. |
| 8,647,326 B2 | 2/2014 | Solomon et al. |
| 8,721,627 B2 | 5/2014 | Alpert |
| 8,832,894 B2 | 9/2014 | Rogers et al. |
| 8,834,650 B2 | 9/2014 | Rogers et al. |
| 9,072,868 B2 | 7/2015 | Ziebol |
| 9,078,992 B2 | 7/2015 | Ziebol |
| 2001/0003150 A1 | 6/2001 | Imbert |
| 2002/0133124 A1 | 9/2002 | Leinsing et al. |
| 2004/0024357 A1 | 2/2004 | Pelkey et al. |
| 2004/0030321 A1 | 2/2004 | Fangrow |
| 2004/0039341 A1 | 2/2004 | Ranalletta |
| 2004/0171993 A1 | 9/2004 | Bonaldo |
| 2004/0172006 A1 | 9/2004 | Bonaldo |
| 2004/0195136 A1 | 10/2004 | Young et al. |
| 2004/0258560 A1 | 12/2004 | Lake et al. |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0214185 A1 | 9/2005 | Castaneda |

(56) References Cited

U.S. PATENT DOCUMENTS

| | | | |
|---|---|---|---|
| 2006/0030827 | A1 | 2/2006 | Raulerson et al. |
| 2006/0048313 | A1 | 3/2006 | Yamaki |
| 2006/0189961 | A1 | 8/2006 | Miyahara |
| 2006/0253103 | A1 | 11/2006 | Utterberg et al. |
| 2007/0106205 | A1 | 5/2007 | Connell et al. |
| 2007/0106229 | A1 | 5/2007 | Wong |
| 2007/0112333 | A1 | 5/2007 | Hoang et al. |
| 2007/0156118 | A1 | 7/2007 | Ramsey et al. |
| 2007/0176117 | A1 | 8/2007 | Redmond et al. |
| 2008/0019889 | A1 | 1/2008 | Rogers et al. |
| 2008/0027399 | A1 | 1/2008 | Harding et al. |
| 2008/0038167 | A1 | 2/2008 | Lynn |
| 2008/0039803 | A1 | 2/2008 | Lynn |
| 2008/0086091 | A1 | 4/2008 | Anderson et al. |
| 2008/0095680 | A1 | 4/2008 | Steffens et al. |
| 2008/0128646 | A1 | 6/2008 | Clawson |
| 2008/0132880 | A1 | 6/2008 | Buchman |
| 2008/0147047 | A1 | 6/2008 | Davis et al. |
| 2008/0177250 | A1 | 7/2008 | Howlett et al. |
| 2009/0005759 | A1 | 1/2009 | Chelak |
| 2009/0008393 | A1 | 1/2009 | Howlett et al. |
| 2009/0028750 | A1 | 1/2009 | Ryan |
| 2009/0062766 | A1 | 3/2009 | Howlett et al. |
| 2009/0099529 | A1 | 4/2009 | Anderson et al. |
| 2009/0137969 | A1 | 5/2009 | Colantonio et al. |
| 2009/0149819 | A1 | 6/2009 | Chelak |
| 2009/0163876 | A1 | 6/2009 | Chebator et al. |
| 2009/0205151 | A1* | 8/2009 | Fisher ............... A61M 39/162 15/104.04 |
| 2010/0000040 | A1 | 1/2010 | Shaw et al. |
| 2010/0047123 | A1 | 2/2010 | Solomon et al. |
| 2010/0049170 | A1* | 2/2010 | Solomon ............ A61M 39/162 604/539 |
| 2010/0050351 | A1 | 3/2010 | Colantonio et al. |
| 2010/0172794 | A1 | 7/2010 | Ferlic et al. |
| 2010/0174162 | A1 | 7/2010 | Gough et al. |
| 2010/0199448 | A1 | 8/2010 | Vazales et al. |
| 2010/0312197 | A1 | 12/2010 | Sano et al. |
| 2010/0313366 | A1 | 12/2010 | Rogers et al. |
| 2011/0213341 | A1 | 9/2011 | Solomon et al. |
| 2011/0265825 | A1 | 11/2011 | Rogers et al. |
| 2011/0277788 | A1 | 11/2011 | Rogers et al. |
| 2012/0039764 | A1 | 2/2012 | Solomon et al. |
| 2013/0019421 | A1 | 1/2013 | Rogers et al. |
| 2013/0184679 | A1 | 7/2013 | Ziebol |
| 2013/0237911 | A1 | 9/2013 | Von Schuckmann |
| 2014/0101876 | A1 | 4/2014 | Rogers et al. |
| 2014/0228773 | A1 | 8/2014 | Burkholz |

FOREIGN PATENT DOCUMENTS

| | | |
|---|---|---|
| EP | 1061000 A2 | 12/2000 |
| EP | 1977714 A1 | 10/2008 |
| EP | 2135626 A1 | 12/2009 |
| JP | 07-047137 | 2/1995 |
| JP | 07-043674 U | 9/1995 |
| JP | 09-012829 | 1/1997 |
| JP | 09-206370 | 8/1997 |
| JP | 09-206370 A | 8/1997 |
| JP | 2001-527441 A | 12/2001 |
| JP | 2002-291906 A | 10/2002 |
| JP | 4234777 B1 | 3/2009 |
| WO | WO 94/11474 | 5/1994 |
| WO | WO-98/48872 A1 | 11/1998 |
| WO | WO-00/24442 A1 | 5/2000 |
| WO | WO-2007/103998 A2 | 9/2007 |
| WO | WO-2007/137056 A2 | 11/2007 |
| WO | WO-2009/136957 A1 | 11/2009 |
| WO | WO-2009/153224 A1 | 12/2009 |
| WO | WO-2011/056221 A1 | 5/2011 |
| WO | WO-2011/120017 A1 | 9/2011 |

OTHER PUBLICATIONS

U.S. Appl. No. 60/832,437, filed Jul. 21, 2006, Rogers.

Byington "Spontaneously Generating Life in Your Classroom? Pasteur, Spallanzani & Science Process," *The American Biology Teacher*, vol. 63, No. 5 (May 2001). pp. 340-345. Published by University of California Press on behalf of National Association of Biology Teachers.

European Patent Office, European Search Report and Opinion for EP Application No. EP 10 78 3956, date of completion of the search Mar. 12, 2014, 7 pgs.

European Patent Office, Supplementary Partial European Search Report and Opinion for EP Application No. 07 75 8117 date of completion of the search Nov. 22, 2012, 6 pgs.

International Search Report and Written Opinion dated Jul. 22, 2009, PCT/US2008/053744.

International Search Report and Written Opinion dated Nov. 9, 2012, PCT/US2012/025517.

International Search Report and Written Opinion issued in International Application No. PCT/US2014/026716, dated Jun. 12, 2014.

International Standard ISO 594-2. "Conical Fitting with 6% (Luer) Taper for Syringes, Needles and Certain Other Medical Equipment—Part 2: Lock Fittings". Reference No. ISO 594-2:1998(E). *Second edition*. (Sep. 1, 1998)1:11.

Japanese Patent Office, Japanese Notice of Reasons for Rejection for Japanese Patent Application No. 2008-558527 dated Apr. 12, 2012.

Japanese Patent Office, Japanese Notice of Reasons for Rejection for Japanese Patent Application No. 2008-558527 dated Apr. 2, 2013.

Material Properties of Polyamide (Nylon), www.madeitfrom.com, pp. 1-2. Retrieved Sep. 23, 2012.

Material Properties of Polycarbonate, www.madeitfrom.com, pp. 1-3. Retrieved Sep. 23, 2012.

Material Properties of Polypropylene, www.madeitfrom.com, pp. 1-2. Retrieved Sep. 23, 2012.

Menyhay et al. "Disinfection of Needleless Catheter Connectors and Access Ports with Alcohol May Not Prevent Microbial Entry: The Promise of a Novel Antiseptic-Barrier Cap". *The University of Chicago Press on behalf of The Society for Healthcare Epidemiology of America. Infect Control Hosp Epidemiol* vol. 27(2006):23-27.

Menyhay Healthcare Systems LLC available at http://www.menyhaymedical.com/menyhay.html (retrieved Nov. 8, 2013).

PCT Search Report and Written Opinion dated Oct. 16, 2013 for PCT application No. PCT/US2013/044167.

The International Bureau of WIPO, PCT International Preliminary Report on Patentability and Written Opinion of the International Searching Authority for International Application No. PCT/US2007/063534 dated Nov. 21, 2007.

Value Plastics Inc, Luer Connectors, http://www.valueplasctics.com/search/search.aspx, pp. 1-2. Retrieved Sep. 23, 2012.

U.S. Appl. No. 12/205,408, filed Sep. 5, 2008, US 2010-0292673.
U.S. Appl. No. 13/099,324, filed May 2, 2011, US 2011-0265825.
U.S. Appl. No. 13/466,976, filed May 8, 2012, US 2012-0216360.
U.S. Appl. No. 13/844,687, filed Mar. 15, 2013, US 2014-0261581.
U.S. Appl. No. 13/910,053, filed Jun. 4, 2013, US 2014-0150832.
U.S. Appl. No. 14/484,708, filed Sep. 12, 2014, US 2015-0000061.
PCT/US2014/026716, filed Mar. 13, 2014, WO 2014-151949.
U.S. Appl. No. 12/205,480, filed Sep. 5, 2008, US 2010-0292673.
PCT/US2013/044167, filed Jun. 4, 2013, WO 2013-184716.
U.S. Appl. No. 12/791,809, dated Jun. 1, 2010, US 2010-0306938.
U.S. Appl. No. 13/072,653, dated Mar. 25, 2011, US 2011-0232020.
U.S. Appl. No. 13/553,627, filed Jul. 19, 2012, US 2013-0019421.
U.S. Appl. No. 14/107,458, filed Dec. 16, 2013, US 2014-0101876.

* cited by examiner

FEMALE LUER CONNECTOR DISINFECTING CAP

CROSS-REFERENCE TO RELATED APPLICATIONS

This application is a continuation of U.S. application Ser. No. 14/285,526, filed May 22, 2014, now pending, which is a divisional of U.S. application Ser. No. 13/099,324, filed May 2, 2011, issued as U.S. Pat. No. 9,259,284, which claims priority to U.S. Provisional Application No. 61/330,243, filed Apr. 30, 2010, the disclosures of which are incorporated by reference in their entirety herein.

BACKGROUND

The present invention relates to cleaning devices, and more particularly to a universal connector cap capable of cleansing a connector of pathogens or other harmful materials or contaminants, for example by employing a friction-based fitting to a connector site or other medical implement.

In the medical field, there is often a need to connect tubing to a variety of devices to facilitate the administration of fluids to a patient. To allow tubing and components from different manufacturers of a variety of devices to connect with one another, a standard connector type was developed. The connector type generally consists of a male connector (or "port," which is used interchangeably herein) being inserted into a female connector whereby friction can keep them together. The taper of the male connector can be adapted to closely match the taper of the female connector to create a friction or compression type connection that is fluid tight. For infusion or aspiration of fluids to or from an intravenous or arterial access line or device, i.e. including, without limitation, a catheter, IV set, extension set stopcock, syringe, valve, etc., this type of connector is known as a Luer fitting, a Luer connector, a Luer lock, or the like. The dimensions of Luer connectors, which are referred to herein generically as a "Luer" or "Luers," can be found in ISO Standards 594-1 and 594-2.

Luers were later improved with threading mechanisms to allow and assist the two connectors to screw together, whereby friction was again the holding force. This threading was merely an enhancement to enable a user to more easily drive the male and female connectors together. If a female port remains open when not connected, there is an increased risk of infections, leakage of fluid and other problems resulting from having open access to the patient. To eliminate this "open" problem, a rubber port can be used for the female connector that can keep the female port closed until used for injections. The rubber port was typically pierced with a needle, or can be removed to connect the female connector with other tubing.

The female connector was further improved with one of several other features, such as a split septum, biased septum, displaceable piston etc. that can be displaced from a closed position by the male connector when it needs to be out of the way, but which can spring back to the closed position as required. This device was highly desirable because it eliminated the dangerous needle and its closure was automatic. This device is commonly called a needleless adapter, or a Luer Activated Valve (LAV). For instance, the Luer tapered male port on standard syringes can open a fluid path without a needle, through or around the displaced feature on the female side when the two were pressed or screwed together. After the injection of fluids, the syringe was unscrewed/removed. Upon removal, the needle-free feature (whether a biased plug/piston, split septum or other displaceable construct) is, without user interaction, automatically biased back into its normally closed position.

This improvement simplified the administration of fluids by removing needles and reducing open port risks but still necessitated the use of a disinfecting wipe prior to insertion since the outside features of the connection can still remain exposed to touch and air contamination.

SUMMARY

This document describes features of cleaning devices for medical implements as well as methods for using such devices. In one aspect, a cleaning device includes a cap having an opening to an inner cavity. The opening is adapted to receive a site of the medical implement. The inner cavity includes a male Luer protrusion that extends up from an inner wall toward the opening, and is sized and adapted for insertion into a female Luer when the cap is provided on the medical implement. The cleaning device further includes a compressible cleaning material that surrounds the male Luer protrusion and that contains a cleaning agent prior to receipt of the site of the medical implement, i.e. the cleaning material is pre-loaded with the cleaning agent. The compressible cleaning material is at least partially secured in the inner cavity and adapted to swab and clean the site with the cleaning agent, including cleaning the female Luer and inner lumen therein.

The cap can further include a friction-forming member for creating a friction-based fitting of the cap onto the site of the medical implement. Alternatively, the cap further includes a member, for example one protruding from threading at the opening of the inner cavity, that, once the cap is fitted onto the site of the medical implement, inhibits easy removal of the cap until a force exerted on the cap exceeds a certain threshold of force. The cap can further include one or more energy directors on which a threaded ring is mated to a receptacle in the cap. The cap can be filled with a cleaning material and cleaning solution, such as a foam pad with an antibacterial or antimicrobial solution. Alternatively, the cap can be filled with a gel, foam or wax that includes an antibacterial or antimicrobial component.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

When feasible, like reference symbols in the various drawings indicate like elements.

DETAILED DESCRIPTION

Figure 1:
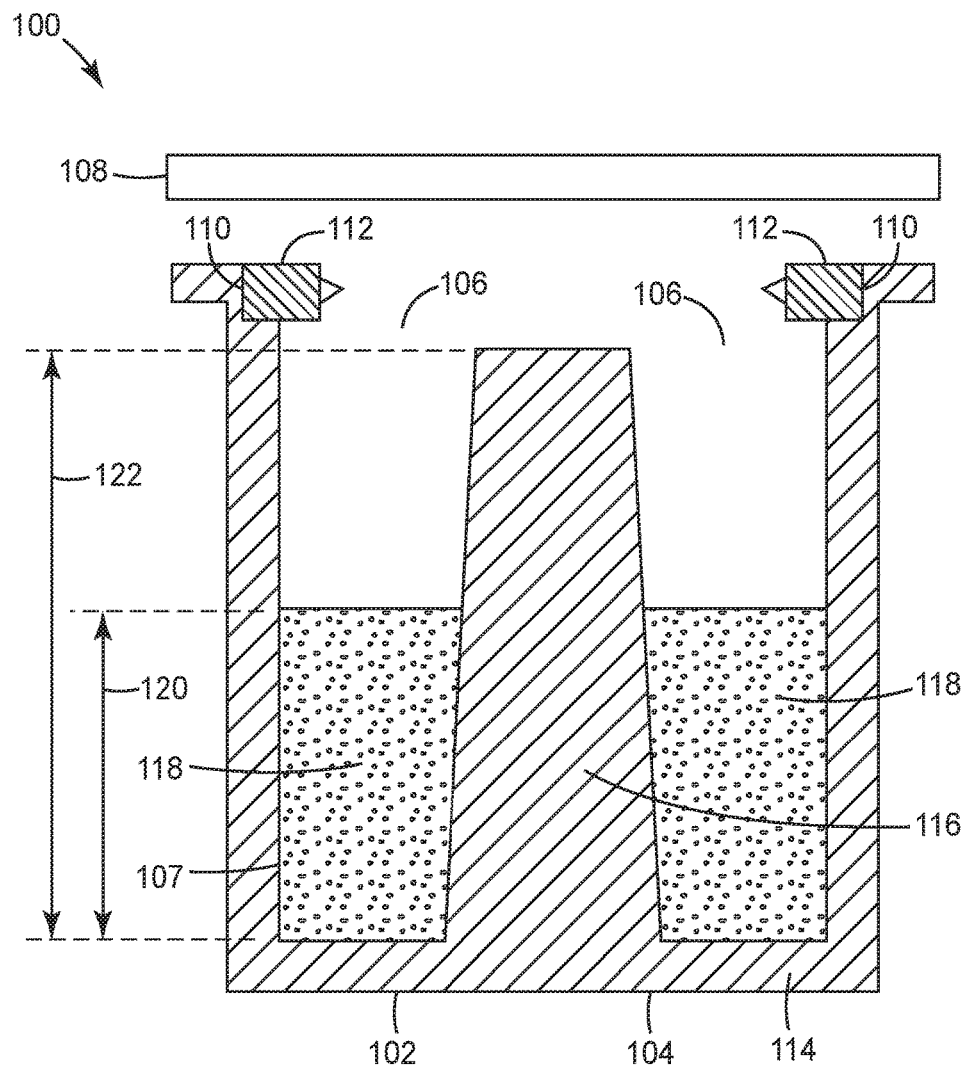
FIG. 1 shows a male cleaning device.

An improved cleaning device has been created that acts as a combination cap and disinfecting swab whereby it screws on or is otherwise fitted onto the closed female side of a Luer activated valves (i.e. LAV). The cleaning device contains features to disinfect or sterilize the external surface of the closed female port, and further protects the surface from further contamination as long as it remains fitted on to the female port. The cleaning device includes the male feature, i.e. the tapered cone or tapered cylinder, to open the female Luer valve as well as clean the outer and inner surfaces of the Luer valve around the septum. Luer activated valves are typically made of very rigid plastics such as polycarbonate or acrylic. The female connection of the Luer has threads and a root diameter.

A cleaning device in the form of a cap to clean the female connection can be provided as exemplified in U.S. patent application Ser. No. 11/705,805, filed Feb. 12, 2007, the contents of which are incorporated herein by reference for all purposes. The cleaning device for a medical implement includes a cap having an opening to an inner cavity. An inner surface of the opening includes one or more threads adapted to receive a site of the medical implement. The cleaning device further includes a cleaning material formed of a compressible material that is at least partially secured or supported in the inner cavity. The cleaning material contains a cleaning agent that effectively eliminates pathogens and other harmful materials from the site and that can be activated from the cleaning material by twisting and fitting the cap onto the site, particularly if the cap is fitted onto the site for a period of time.

The one or more threads of the cleaning device can be provided by a threaded ring adapted to be fixedly positioned at the inner surface of the opening of the cap. Two threads encircle approximately one-quarter to one-half of the inner surface of the threaded ring. A tab extends from each thread, preferably at the lower terminus of each thread. The tab can be made thinner than the rest of the thread, to allow flexure or bending. The threaded ring can be formed by plastic injection molding. The threads are formed such that the threaded ring does not need to be unwound during molding or fabrication. The tabs of each thread engage with the outer threading of a valve or port, and any gap provided thereby allows for compatibility with many sized valves or ports, as well as allows limited evaporation of cleaning solution (such as isopropyl alcohol) that might be inside the cap.

The tabs create friction on one or both outer sides of the female connection of the Luer, thereby preventing the cap from unscrewing from the female connection of the Luer. In some implementations, the threads of the cap correspond to an ISO Luer Standard thread. Each tab presses against the root diameter of the female Luer and presses on the sides of the thread feature of the female connection, thereby creating friction. The threading and one or more protrusions cooperate to create a compression fit and to prevent the cap from accidentally coming off the site onto which it is fitted.

The threads of the cap, and/or the protrusions of added material, can be made of a softer, more compressible material than the cap or the female connector, such as another type of plastic or a rubber, etc. The features pressing on the female side can work in several ways. The added material can press against the more rigid female LAV root or body or threads to create friction. The added material can also displace plastic to create a single use scenario, where the part pressing on the thread pushes against the outside of the thread or on the sides of the thread. The material can further deflect in a variety of ways to make putting on simple, and taking off more difficult.

Additionally the cap can be configured for being pressed on instead of, or in addition to, being screwed on, with material that protrudes from the inner ring or threads of the cap to press against the threads or roots of the female connection of the LAV, similar in function to a star retaining washer. It can have simple features on the press parts that create resistance when pulled off. The protruding "flaps" can be bendable to allow the cap to be forced over the female threads. Once past the threads or a section of threads, the "flaps" can naturally return to their unbent state to prevent the inadvertent removal of the cap. To remove, it may be possible to unscrew the cap where the flaps find the thread track, but the user can just pull off the cap upon exceeding a certain threshold force to overcome the resistance by the added material and/or the threads of the cap.

FIG. 1 shows a cleaning device 100, including a cap portion 102 that includes a cap 104 with an opening 106 to an interior cavity 107. The cap 104 can be formed of rigid plastic, such as high density polyethylene (HDPE) plastic. A removable foil lid 108 is adapted to close the opening 106, and can be sealed on the top outer periphery of the opening 106 by a heat or thermal process. The opening 106 is slightly wider in diameter than the rest of the interior cavity 107 to form a ring receptacle 110 and to be able to receive a threaded ring 112 as described above. The threaded ring 112 can be ultrasonically welded, glued, or otherwise attached into the receptacle 110. The ring receptacle 110 includes a number of energy directors in the form of bumps or protrusions that enable welding or bonding of the threaded ring 112 into the ring receptacle 110. The energy directors also stabilize the threaded ring 112 for proper alignment and mounting, and can resist against turning the threaded ring 112 relative to the cap 104 when the cleaning device 100 is screwed on or otherwise applied to a port or valve.

The top interior wall 114 of the cap 104 includes a male luer protrusion 116 extending up toward the opening 106 of the cap 104, preferably formed as a portion of a tapered cone or cylinder. The male Luer protrusion 116 is ringed by cleaning material 118 formed of a compressible material that is at least partially secured in the inner cavity 107. The depth or height 120 of the cleaning material can be varied, but in preferred implementations the compressible cleaning material is at least the same or shorter height than height 122 of the top of the male luer protrusion 116.

The top interior wall 114 of the cap 104 can have one or more protrusions 116 extending up from the interior wall 114 toward the opening 106 of the cap 104. The one or more protrusions 116 can be used to support a cleaning material 118 such as foam, cotton, or other porous material, or provide stability to a thixotropic cleaning solution as an alternative. The cleaning material exists in the form of a doughnut. In some implementations, the one or more protrusions 116 can be formed of a flexible material to contact and scrub the forward face of a valve or port, such as the septum of a valve.

The cleaning device 100 provides many advantages. For example, the cleaning device 100 can be easily manufactured. The cleaning device 100 can be easily fit on appropriate devices, such as machines. Further, the cleaning device 100 can be manufactured such that the cleaning device 100 fits any Luer thread. The cleaning device can use different tools for threading. When using a dialysis tube, an inner lumen of the hub, outside threads, and the face of hub can optionally also be disinfected. Cores can be redesigned using a custom tool to obtain new design caps. Length and wings can be added to obtain a new tool for the cap. The new tool can be a further enhancement to an existing tool.

Figure 2:
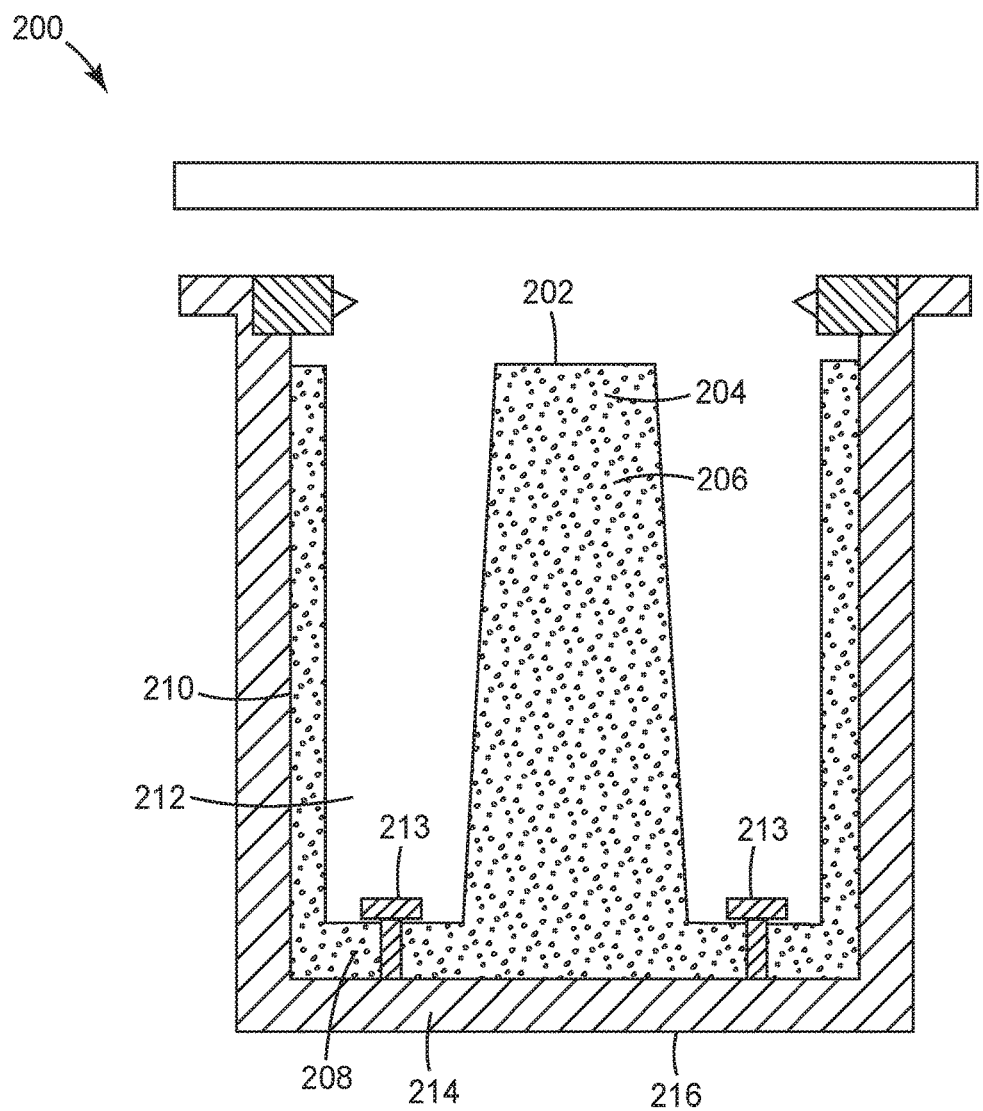
FIG. 2 shows a variation of a cleaning device.

FIG. 2 shows an alternative implementation 200 of a cleaning device, similar to the device 100 shown in FIG. 1, in which the male Luer protrusion 202 is formed of a plug of a cleaning material (e.g. foam, cotton, or other porous material) 204 that is preloaded with a cleaning agent 206 such as isopropyl alcohol. The cleaning device 200 has a high confidence level of reducing or eliminating infection. The plug 204 can include the protrusion 202 ringed by a channel 208, and can also include side walls 210 surrounding the outside of the channel 208. The plug 204 can be secured into the interior cavity 212 of the cap by posts 213, by adhesive, or by a series of barbs that extend up from the top interior wall 214 of the cap 216. The posts 213 can be molded by a heat-staking process. Any damage by heat staking can be prevented or minimized by using suitable techniques.

Figure 3:
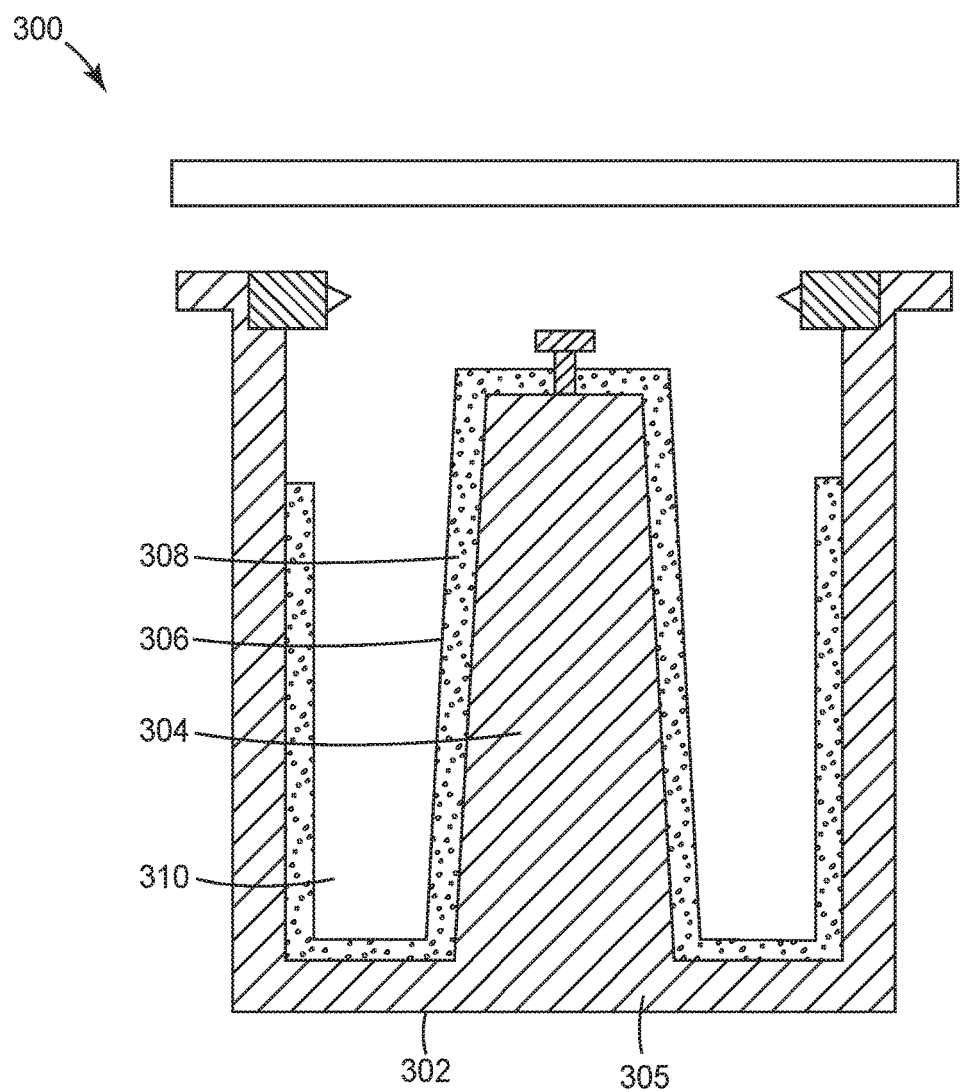
FIG. 3 shows yet another variation of a cleaning device.

FIG. 3 shows another implementation 300 of a cleaning device, combining certain features from the devices (100, 200) shown in FIGS. 1 and 2. The cap 302 is similar to the caps 104, 216, but the male Luer protrusion 304 can be integral with the cap material 305, i.e. formed of a single mold. A molded "skin" of foam or some other cleaning material layer 308 is overlaid on some or most of the surface of the interior cavity 310, including the male luer protrusion 304. The skin 306 can be soaked with a cleaning agent 308, of a calculated amount to clean the inside and outside surfaces of the female port near the septum. The male luer protrusion 304 provides a seal with the inner lumen of the female luer port. The skin 306 can be thermally bonded, glued, riveted or otherwise attached to the cap material 305.

The inner cavity of the cap (104, 216, or 302) can include a cleaning material laden with a cleaning solution. In some implementations, the cleaning material is a foam material, and the cleaning solution is a liquid that saturates the foam material. Suitable cleaning solutions include isopropyl alcohol, ethyl alcohol, CHG, choloroxylenol (PCMX), providone iodine, etc. The cleaning solution can also include emollients or other components.

In other implementations, the cleaning material and cleaning solution can be formed of a thixotropic substance such as a gel or foam, or of a fluid with high viscosity. The thixotropic substance can include a base viscous substance impregnated with a cleaning solution in a manner to maintain at least a certain degree of viscosity. The thixotropic substance can at least partially fill the interior cavity of the cap (104, 216, or 302), and flow around the valve or port to cover a desired surface area when the cap (104, 216, or 302) is placed on the valve or port.

Figure 4:
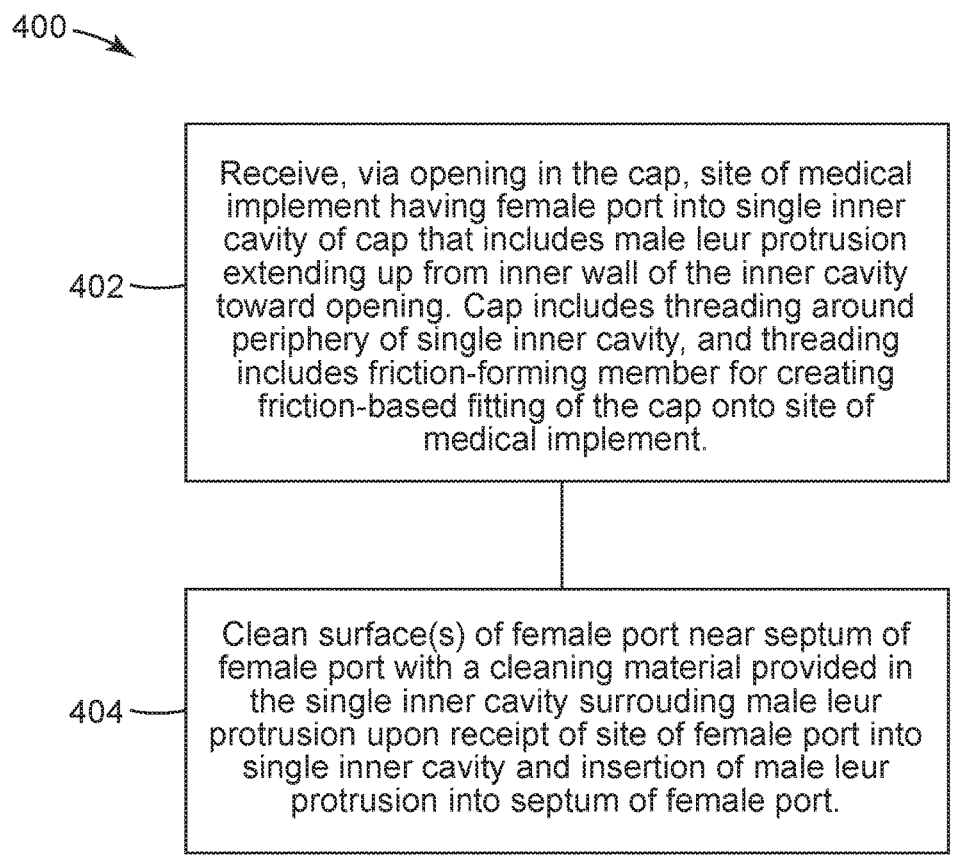
FIG. 4 shows a process flow chart showing at least one feature consistent with an implementation of the current subject matter.

FIG. 4 shows a process flow chart 400 showing at least one feature consistent with an implementation of the current subject matter. At 402, an opening of a cap receives a site of a medical implement having a female port. The cap has an outer surface including a plurality of vertical ridges on the outer surface while the opening provides access to a single inner cavity that includes a male luer protrusion extending up from an inner wall of the inner cavity toward the opening. The cap also includes, around a periphery of the single inner cavity, threading including a friction-forming member for creating a friction-based fitting of the cap onto the site of the medical implement. At 404, a cleaning material, which includes a cleaning agent and is provided in the single inner cavity surrounding the male luer protrusion upon receipt of the site of the female port into the single inner cavity and the insertion of the male luer protrusion into the septum of the female port, cleans at least one surface of the female port near a septum of the female port.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

The invention claimed is:

1. A cleaning device comprising:
   a cap having an opening to an interior cavity, the interior cavity defined by an interior wall that includes a male Luer protrusion extending in the direction of the opening from an end of the interior cavity opposite the opening; and
   a skin of cleaning material overlaid on at least a portion of the interior wall.

2. The cleaning device of claim 1, further comprising a cleaning agent, wherein the cleaning agent impregnates the cleaning material.

3. The cleaning device of claim 2, wherein the cleaning agent comprises at least one of isopropyl alcohol, ethyl alcohol, chlorhexidine gluconate (CHG), chloroxylenol (PCMX), and povidone iodine.

4. The cleaning device of claim 1, wherein the cleaning material is a porous material.

5. The cleaning device of claim 1, wherein the cleaning material is a thixotropic substance.

6. The cleaning device of claim 1, wherein the skin of cleaning material is at least partially secured to the interior wall by at least one of a thermal bond, glue and rivet.

7. The cleaning device of claim 1, further comprising a second cleaning material.

8. The cleaning device of claim 1, wherein the male Luer protrusion has a frustoconical shape that decreases in diameter towards the opening.

9. The cleaning device of claim 1, wherein the male Luer protrusion is dimensioned for at least partial insertion in a lumen of a female port.

10. The cleaning device of claim 9, wherein the cleaning device cleans at least a portion of inside and at least a portion of outside surfaces of the female port.

11. The cleaning device of claim 1, wherein the male Luer protrusion does not extend beyond the opening of the cap.

12. The cleaning device of claim 1, further comprising at least one friction forming protrusion that extends outward from a portion of the interior wall near the cap opening, wherein the portion of the interior wall from which the friction forming protrusion extends does not form part of the male Luer protrusion.

13. The cleaning device of claim 12, wherein the friction forming protrusion comprises at least one thread.

14. The cleaning device of claim 13, further comprising a tab that extends from a lower terminus of each thread.

15. The cleaning device of claim 12, wherein the friction forming protrusion is a bendable flap.

16. The cleaning device of claim 12, wherein the friction forming protrusion is made of a softer material than that used to make the interior wall.

17. The cleaning device of claim 1, further comprising a threaded ring that is attached to the interior wall near the opening.

18. The cleaning device of claim 1, wherein the cleaning material is compressible.

19. The cleaning device of claim 18, wherein the interior wall is formed from a rigid material.

20. The cleaning device of claim 1, further comprising a removable seal that completely covers the opening.

* * * * *